US010390598B2

(12) United States Patent
Aussant et al.

(10) Patent No.: US 10,390,598 B2
(45) Date of Patent: Aug. 27, 2019

(54) ELASTIC CLOTHING OR ACCESSORY TREATED WITH MICROENCAPSULATED SUBSTANCE AND HAVING CONSUMER-ACTIVATED PULL MECHANISM

(71) Applicant: Conscious Creations, LLC, Newburyport, MA (US)

(72) Inventors: Laura Aussant, Newburyport, MA (US); Paul Dahn, Newburyport, MA (US)

(73) Assignee: Conscious Creations, LLC, Newburyport, MA (US)

( * ) Notice: Subject to any disclaimer, the term of this patent is extended or adjusted under 35 U.S.C. 154(b) by 473 days.

(21) Appl. No.: 15/165,146

(22) Filed: May 26, 2016

(65) Prior Publication Data

US 2016/0345704 A1 Dec. 1, 2016

Related U.S. Application Data

(60) Provisional application No. 62/167,561, filed on May 28, 2015.

(51) Int. Cl.
| *A61K 8/11* | (2006.01) |
| *A61K 9/48* | (2006.01) |
| *A01M 29/12* | (2011.01) |
| *A45D 34/02* | (2006.01) |
| *A45D 8/34* | (2006.01) |
| *A61K 8/02* | (2006.01) |
| *A45D 8/00* | (2006.01) |

(52) U.S. Cl.
CPC ............... *A45D 8/34* (2013.01); *A01M 29/12* (2013.01); *A61K 8/0204* (2013.01); *A61K 8/11* (2013.01); *A61K 9/48* (2013.01); *A41B 2400/36* (2013.01); *A45D 34/02* (2013.01); *A45D 2008/004* (2013.01)

(58) Field of Classification Search
None
See application file for complete search history.

(56) References Cited

U.S. PATENT DOCUMENTS

| 5,232,769 A | * | 8/1993 | Yamato | A41B 17/00 2/239 |
| 5,826,598 A | | 10/1998 | Meehan | |
| 7,204,207 B2 | * | 4/2007 | Hurwitz | A01K 27/006 119/795 |
| 2002/0139140 A1 | * | 10/2002 | Schaab | A44C 15/002 63/3 |
| 2011/0257616 A1 | * | 10/2011 | Lakso | A61F 13/2051 604/359 |
| 2015/0164195 A1 | * | 6/2015 | Elliott | A45D 8/34 132/273 |

FOREIGN PATENT DOCUMENTS

WO 00/15072 3/2000

OTHER PUBLICATIONS

Kawasaki et al., Journal of The Textile Machinery, 19(4), pp. 122-127. (Year: 1966).*
Saraf et al., Microencapsulation at an Affordable Price, International Dyer, Sep. 2007, pp. 35-38.
Cheng et al., Imparting Cosmetic Effects on Textiles, Colourage, Aug. 2008, pp. 68-78.

* cited by examiner

*Primary Examiner* — Abigail Vanhorn
(74) *Attorney, Agent, or Firm* — Andrus Intellectual Property Law

(57) ABSTRACT

An elastic textile is treated with a microencapsulated substance and a graspable pull mechanism is attached to the elastic textile. When a consumer pulls the pull mechanism to stretch the elastic textile from a natural relaxed state or a semi-stretched state microencapsulated substance is released. The microencapsulated substance can be fragrance, insect repellant, deodorant or a variety of other substances or combination of substances that are desirable to be released on demand by stretching the elastic textile.

11 Claims, 4 Drawing Sheets

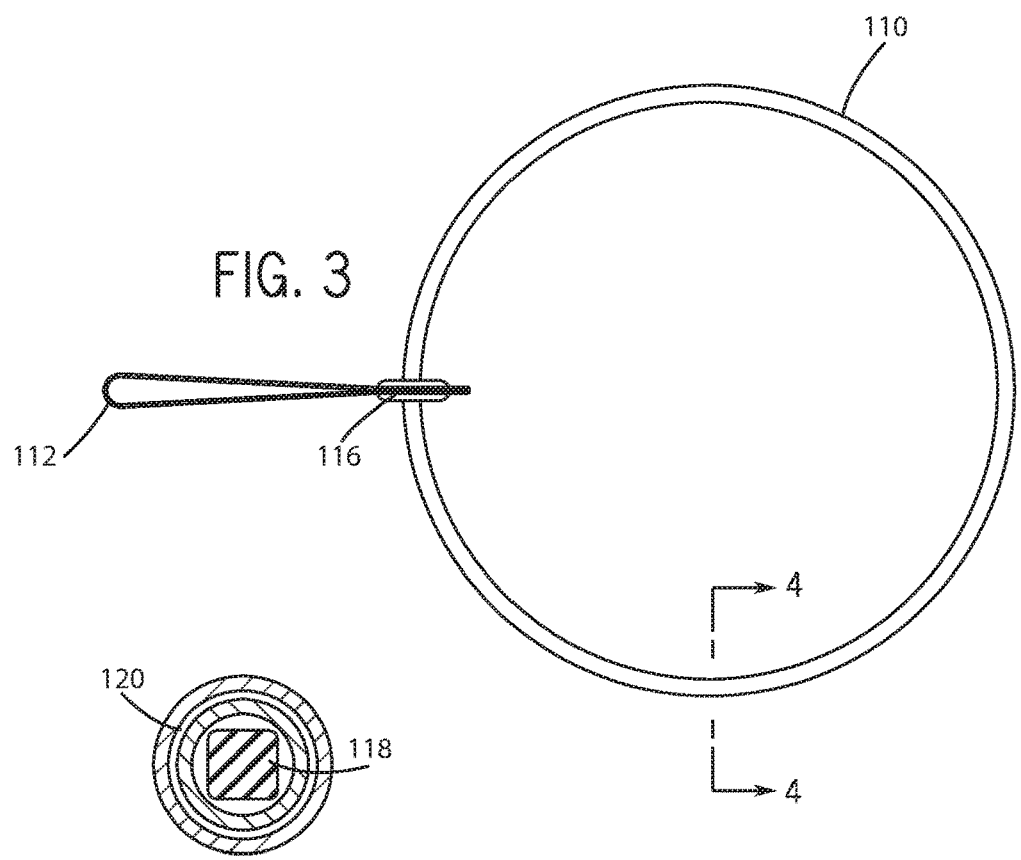
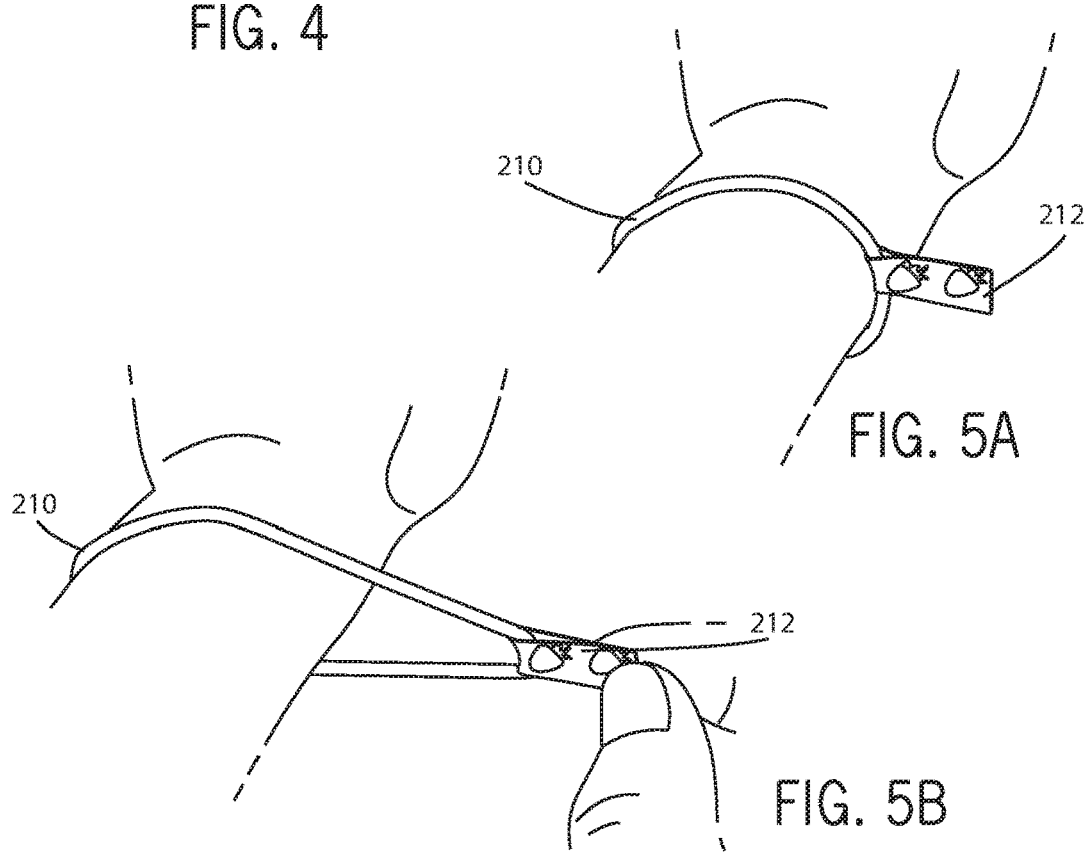

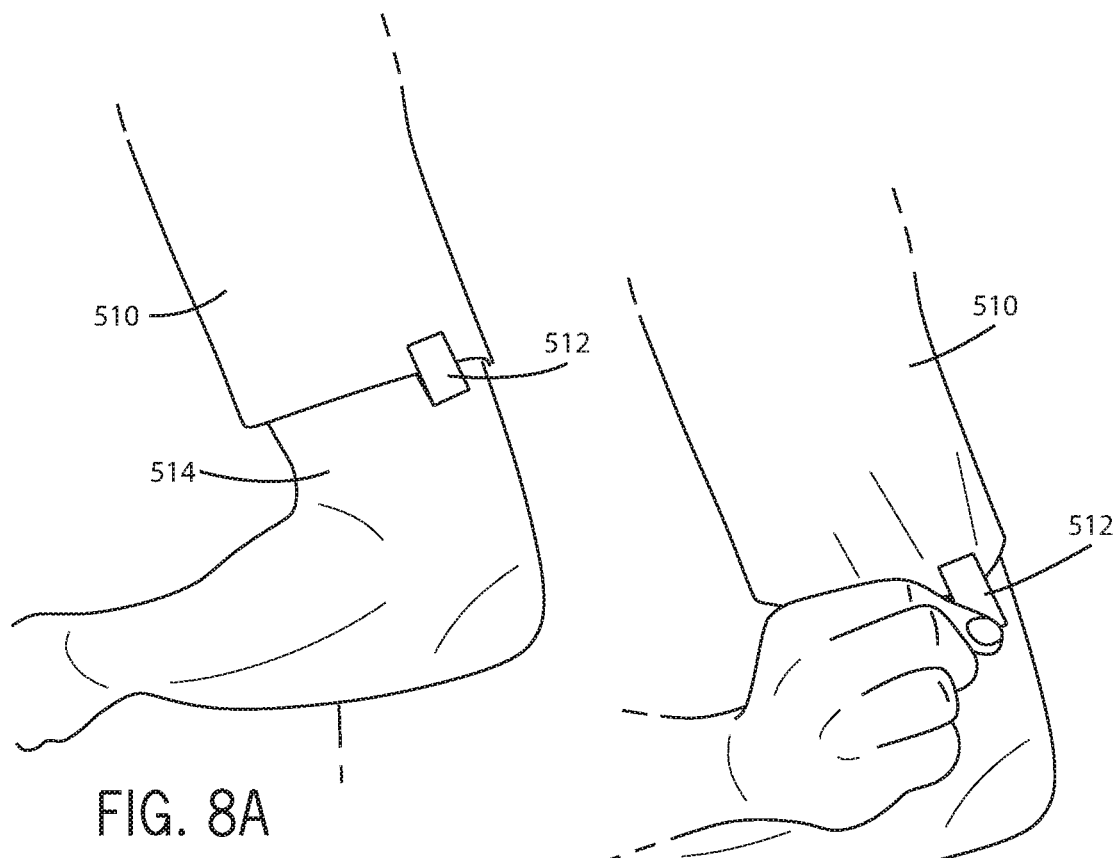
FIG. 8A
FIG. 8B
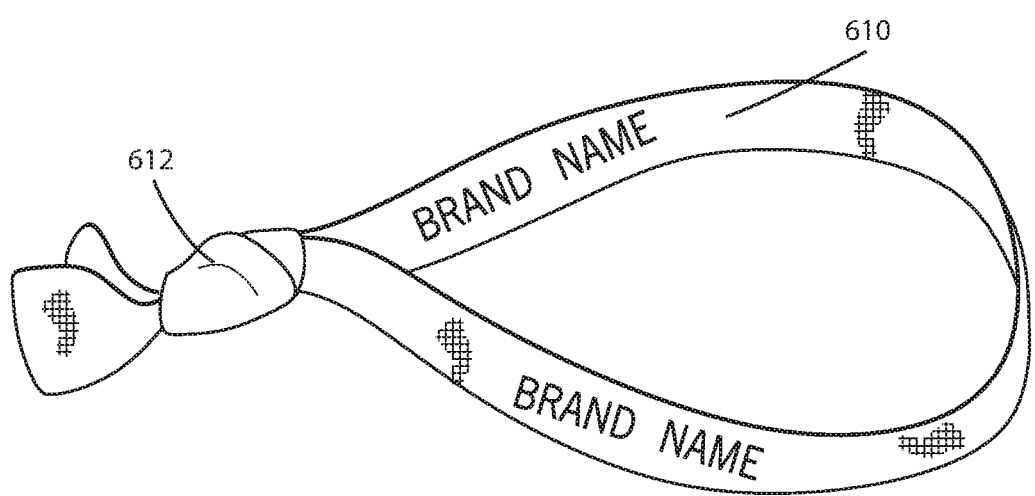
FIG. 9

ELASTIC CLOTHING OR ACCESSORY TREATED WITH MICROENCAPSULATED SUBSTANCE AND HAVING CONSUMER-ACTIVATED PULL MECHANISM

FIELD OF THE INVENTION

The invention relates to elastic textiles treated with microencapsulated substance and the attachment of an easily graspable, consumer-activated pull mechanism. The microencapsulated substance is released from the elastic clothing or accessory when the user pulls on the pull mechanism. The elastic may be housed within a textile (e.g., yarn or thread woven around elastic) or the elastic may be a component of the textile itself. (e.g., 90% cotton, 10% spandex).

BACKGROUND OF THE INVENTION

Various attempts have been made through the years to provide fragrance, scents, repellents or other solutions to clothing, hair accessories and other textiles. Examples include U.S. Pat. No. 5,826,598 entitled "Scented Hair Accessory" and WO 2000/015072 entitled "Scented Scrunchie." The '598 patent includes a chamber located within a tubular housing into which scenting material is placed. The WO '072 patent application places scented formulas inside an elasticized tube placed inside a hair scrunchie. The scented formulas are applied to absorbent materials such as vermiculite or dried flowers and are then placed into the elasticized tube. The scrunchie can be used for tying back hair, adding fragrance. The WO '072 patent application explains that insect repellant or other substances can be placed inside the elasticized tube instead of a scented formula.

It is also known in the textile industry to apply microencapsulated substances to textiles. Microencapsulation is a process of enclosing a substance inside a miniature capsule. There are a variety of microencapsulation techniques such as those described in "Microencapsulation at an Affordable Price" by Dr. Saraf et al., September 2007, *International Dyer*, pp. 35-38; and "Imparting Cosmetic Effects on Textiles" by S. Y. Cheng, et al., August 2008, *Colourage*, pp. 68-78. As disclosed in these two articles, there are not only a variety of ways of applying microencapsulated substances to various products including textiles, but a variety of substances having different properties can be applied to textiles using microencapsulation techniques. For example, fabric can be treated with many kinds of microencapsulated substances including: fragrance or freshener, aloe or other products that make the textile feel smooth or soft, antimicrobial finishes, insect repellant, and even photochromatic or thermochromatic dyes.

SUMMARY OF THE INVENTION

The invention utilizes an easily graspable consumer-activated, pull mechanism attached to an elastic clothing or accessory item treated with a microencapsulated substance. Clothing has been treated with microencapsulated substances in the past; however, the use of a consumer-activated, pull mechanism to release the microencapsulated substance on demand is believed to be novel. By marrying an easily graspable pull mechanism with the treated clothing or accessory, one can conveniently and in a roughly controlled fashion release the substance on demand by pulling the pull mechanism.

More specifically, the invention is an elastic textile to which a microencapsulated substance has been applied in at least a region of the elastic textile. A graspable pull mechanism is attached to the elastic textile so that microencapsulated substance is released when the pull mechanism is pulled to stretch the elastic textile from its natural relaxed state (or a semi stretched state). In this way, the user releases some of the microencapsulated substance on demand. The pull mechanism can take several forms including but not limited to a sewn or glued on pull tag or button, a loosely attached bead, a grommet attached pull tag, or even a knot in the elastic textile. The elastic textile can also take many forms including textiles in which an elastic component is surrounded by a fabric, or an elastic textile in which the elastic is woven into the fabric. The microencapsulated substance may be a fragrance, a deodorant, insect repellant or any other microencapsulated substance in which it may be desired for a consumer to release a portion of it on demand by stretching the elastic textile. Ensuring there is adequate wet pickup of the microencapsulated substance is an important aspect of the invention. In general, the wet pick up percentage of fragrance used for hair ties needs to be higher than for other textiles. The small surface area of the elastic hair ties in particular requires a high thread count of the fabric surrounding the elastic to ensure adequate wet pickup. With the adequate ratio of fragrance to surface area, the microencapsulated substance should be able to last a minimum of 10-20 washes, and more if a binder or crosslinking agent is used. The figures below show examples of the invention being used in connection with a hair tie, a ribbon or wrist band and a shirt.

BRIEF DESCRIPTION OF THE DRAWINGS

FIG. 3 is a side elevation view of the elastic hair tie in FIG. 1.

FIG. 4 is a cross section of the elastic hair tie shown in FIG. 3, showing a rubber core and the outer layer of braided nylon thread.

FIG. 5A is an illustration of another example of the invention in which the pull mechanism is a folded over tag wrapped around the elastic hair tie.

FIG. 5B is an illustration similar to FIG. 5A showing the consumer pulling on the folded over tag to activate the microencapsulated fragrance.

FIG. 8A is an illustration showing another example of the invention in which a pull mechanism in the form of a tag is attached to an elastic shirt treated with microencapsulated fragrance.

FIG. 8B is an illustration similar to FIG. 8A showing the consumer pulling on the tag to activate the microencapsulated fragrance.

FIG. 9 is an illustration of another example of the invention wherein an elastic band is looped and knotted at one end, and the knot serves as the graspable, consumer-activated pull mechanism to release the microencapsulated fragrance.

DETAILED DESCRIPTION OF EXEMPLARY EMBODIMENTS

Figure 1:
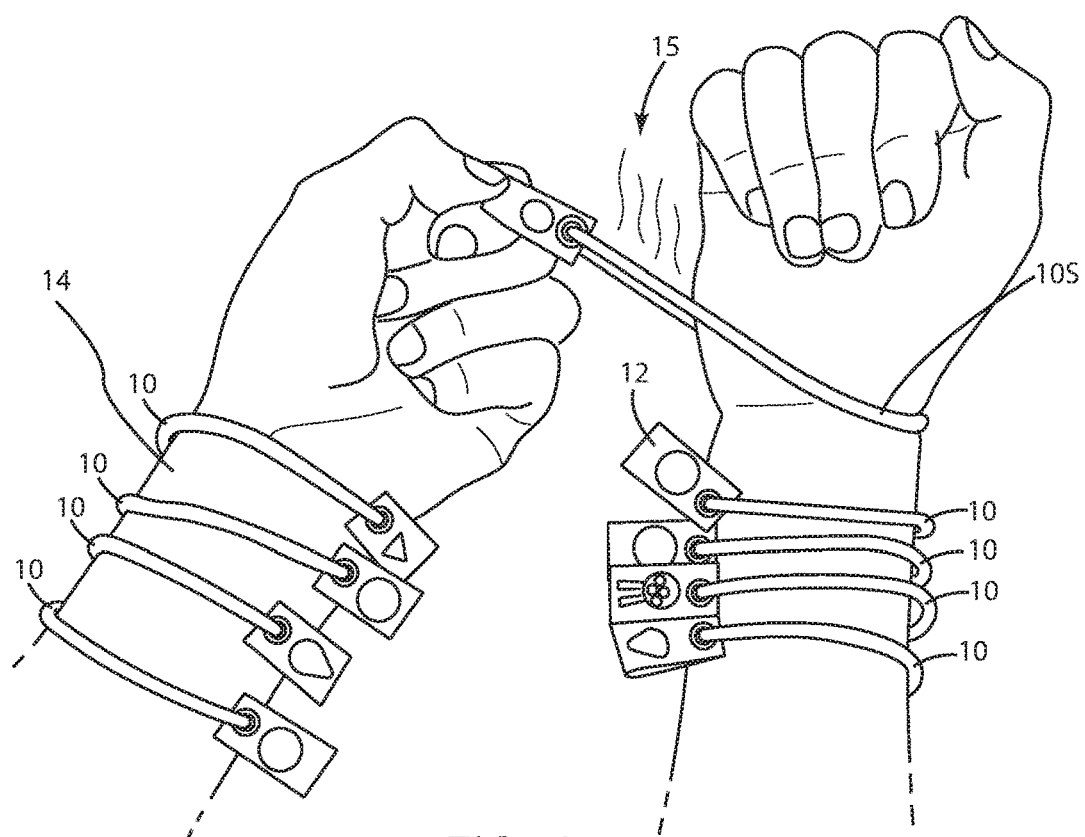
FIG. 1 is an illustration of multiple elastic hair ties around the wrists of a consumer wearing the ties, wherein each hair tie is treated with microencapsulated fragrance having a pull mechanism in the form of a tag.
Figure 2A:
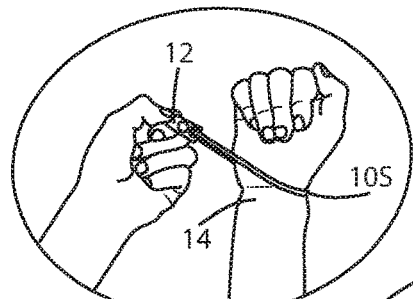
FIG. 2A is an illustration showing the consumer pulling on an elastic hair tie like those shown in FIG. 1 to activate the microencapsulated fragrance.
Figure 2B:
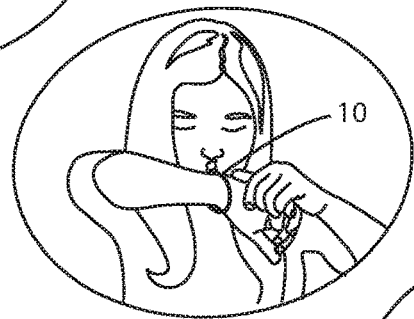
FIG. 2B shows the consumer smelling the fragrance released by the microencapsulated fragrance in hair tie.
Figure 2C:
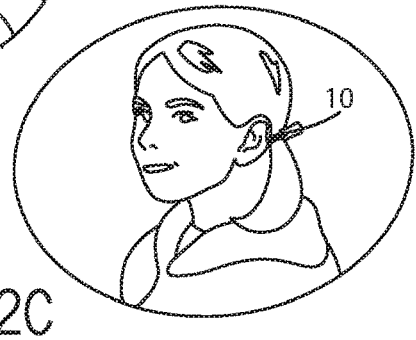
FIG. 2C is an example of the elastic hair tie being worn in the hair by the consumer.

Elastic clothing or accessories treated with a microencapsulated substance and having a graspable, consumer-activated pull mechanism can take several forms. FIG. 1 shows multiple hair ties 10 including pull tags 12, around the wrist 14 of the consumer. The consumer may wish to wear multiple hair ties as shown in FIG. 1 in order to have multiple fragrances. The hair tie 10 includes a circular elastic band with surrounding fabric (e.g., thread) as is generally known in the art. However, in accordance with the invention, the surrounding fabric is treated with a microencapsulated substance (e.g., a fragrance) and the pull tag 12 is attached to the hair tie 10. Other types of pull mechanisms can be used as well in place of the pull tag, such as beads, buttons, knots or other appendage that is easily graspable. FIG. 1 shows multiple hair ties 10 in its natural relaxed state (or a semi-stretched state) around the wearer's wrist 14, and one hair tie 10S being stretched to release some microencapsulated fragrance 15. FIG. 2A shows the consumer pulling on the pull tag 12 to activate microencapsulated fragrance in the stretched hair tie 10S. FIG. 2B shows the consumer smelling the fragrance once it is released from the hair tie 10. FIG. 2C shows the consumer wearing the hair tie 10 in her hair. When the wearer pulls the pull mechanism 12, as shown in FIGS. 1 and 2A, a roughly controlled amount of the microencapsulated substance 15 is released on demand to the surrounding environment for example by rupturing some of the microcapsule walls, or even dissolving or melting some of the microencapsulated walls or by diffusion through some of the microcapsule walls. Treated textiles continue to function after repeated activation because the microcapsules are so small, e.g. the micron level, that some microcapsules remain inactivated on the textile. With the hair ties 10 shown in FIGS. 1 and 2, some of the microencapsulated substance (e.g. fragrance) may be previously released when the hair tie 10 is placed on the wearer's wrist 14, but that does not interfere with the release of additional substance (e.g. fragrance) when the hair tie 10S is further stretched as shown in FIGS. 1 and 2A.

FIG. 3 shows an elevated side view of a hair tie 110 constructed in accordance with one embodiment of the invention. The pull tag 112 in this embodiment is composed of a woven label or hang tag folded over (loop fold) and attached to the elastic band 110 by a metal grommet 116. The pull tag 112 can be of soft durable damask weave or soft woven polyester that is soft and will not irritate the skin. The grommet 116 on this type of pull tag 112 allows the tag to slide freely around the elastic band 110 to permit stretching from multiple places on the elastic, thereby maximizing the utilization of the microencapsulated fragrance over the life of the product. The grommet 116 is attached to the tag 112 through a hole in the tag 112. The band 110 is placed through the grommet 116 and tag 112, and the ends of the band 110 are attached, e.g., by glue, welding, small clasp or other suitable means. FIG. 4 is a cross section of the elastic band 110. The band 110 in this embodiment includes a rubber core 118, surrounded by heavily braided, high-tenacity nylon thread 120. Nylon thread is the preferred wrap for the elastic bands 110 as it returns to its original shape after being stretched to release the microencapsulated fragrance. The rubber core 118 is, e.g., 3 mm in width and 6.5 inches in length. One particularly desirable embodiment contains 16 pieces of heavily braided, high-tenacity nylon thread 120, where the thread size is 70D/2. It is necessary for the nylon braid to be heavy in order to allow for sufficient wet pickup of the microencapsulated fragrance. Polyester thread may be a suitable alternative. However, using natural cotton thread is not desirable because the bands remain stretched when wet, and this complicates the manufacturing process and results in compromised end product that consumers may not find desirable.

FIGS. 5A and 5B illustrate an additional embodiment of the invention where the pull tag 212 is simply folded over the elastic band 210. The pull tag 212 in this embodiment is attached to itself with adhesive or sewn together. When the pull tag 212 is simply folded over the band 210, instead of using a grommet, the pull tag 212 does not move freely around the elastic band 210.

During manufacturing, treatment of the hair tie 210 in FIGS. 5A and 5B with the microencapsulated substance can occur before or after the pull mechanism 212 is attached. For example, since the pull mechanism is a cloth tag 212 it may be simpler to attached the tag 212 prior to treatment. However, depending on the microencapsulation process and the type of pull mechanism used, it might be better to attach the pull mechanism after treatment. For the examples shown in FIGS. 6 and 7, it may be more appropriate to attach the pull mechanism 312, 412 after the textile is treated with the microencapsulated substance. A variety of known treatment methods can be used to apply the microencapsulated substance to textiles in accordance with the invention, e.g. the spray application method, the padding process, the exhaust process, the foaming process, or other known microencapsulation techniques, see above noted publication to Saraf et al, and Cheng et al.

The microcapsules used are small enough that they embed themselves in the strands of thread and also attach topically. The fragrance in most cases will last at least 10-20 washes. A binder or crosslinking agent can be used in certain embodiments in order to increase the longevity of the fragrance. During application of the fragrance it is important to use a high percentage of fragrance per surface area to ensure adequate application of the microcapsules. Using fabric with a high thread count surrounding the elastic bands, as shown in FIG. 4, allows sufficient wet pickup of the microencapsulated fragrance. Determination of the wet pickup can be done by subtracting the wet weight from the dry weight and then dividing the total by the dry weight.

In the example below, the microcapsule shell is composed of melamine resin and is about 2-8 microns in size. The fragrances used can be any number of smells such as strawberry, cotton candy, and bubblegum. However, the fragrances should be safe for inhalation, skin safe, and have high flashpoints.

EXAMPLE

This example explains one desirable method for applying microencapsulated fragrances to a high-tenacity nylon, elastic band. As mentioned above, the high-tenacity nylon threaded, elastic band must have adequate wet pickup of the microencapsulated fragrance. Measured wet pick up percentage is desirably at least 50% where wet pickup is calculated by: 1) weighing the hair tie dry; 2) wetting the hair tie with water and weighing the hair tie; and 3) subtracting the wet weight from the dry weight then dividing by the dry weight. If wet pick up is too low, then more nylon thread needs to be added. Since the elastic hair tie has a small surface area, the wet pick up percentage needs to be higher than on a garment with a larger surface area.

Microencapsulated fragrances were selected to be inhalation and skin safe and to have high flashpoints The microcapsule shell in this example is made of melamine resin, and has a typical capsule size of 2-8 microns. Exemplary fragrance compositions are listed below:

| STRAWBERRY | | |
| --- | --- | --- |
| Chemical Name | CAS # | % |
| Ethyl methylphenylglycidate | 77-83-8 | 15-40 |
| Benzaldehyde, 4-hydroxy-3-methoxy | 121-33-5 | 5-10 |
| 4H-Pyran-4-one, 2 ethyl-3-hydroxy | 4940-11-8 | 3-7 |

| COTTON CANDY | | |
| --- | --- | --- |
| Chemical Name | CAS # | % |
| 4H-Pyran-4-one, 2 ethyl-3-hydroxy | 4940-11-8 | 1-5 |
| Ethyl methylphenylglycidate | 77-83-8 | 1-5 |
| Benzaldehyde, 3-ethoxy-4-hydroxy- | 121-32-4 | 1-5 |
| 1,3-Benzodioxole-5-carboxaldehyde | 120-57-0 | 1-5 |

| BUBBLEGUM | | |
| --- | --- | --- |
| Chemical Name | CAS # | % |
| Benzoic acid, 2-hydroxy-, methyl ester | 119-36-8 | 10-30 |
| Butanoic acid, 3-methylbutyl ester | 106-27-4 | 1-5 |
| Benzaldehyde, 4-hydroxy-3-methoxy | 121-33-5 | 1-5 |
| Benzaldehyde, 3-ethoxy-4-hydroxy- | 121-32-4 | 1-5 |
| Butanoic acid, ethyl ester | 105-54-4 | 0.5-1.5 |
| Oxacyclohexadecan-2-one | 106-02-5 | 0.5-1.5 |
| 1-Butanol, 3-methyl-, 1-acetate | 123-92-2 | 0.5-1.5 |

Testing has shown that the microencapsulated fragrances in this example will last on the high-tenacity, nylon elastic hair ties for a minimum of 10-20 washes.

Figure 6A:
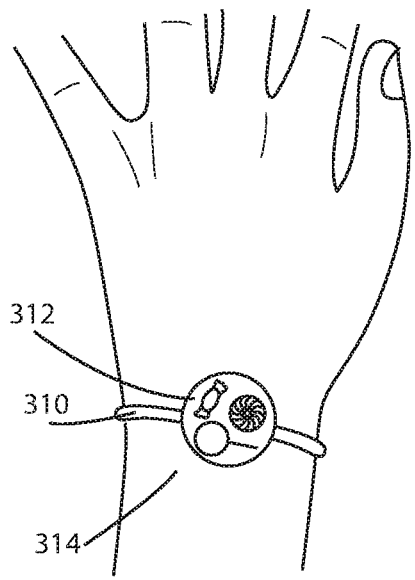
FIG. 6A is an illustration of another example of the invention in which a pull mechanism in the form of a button is attached to an elastic hair tie treated with microencapsulated fragrance.
Figure 6B:
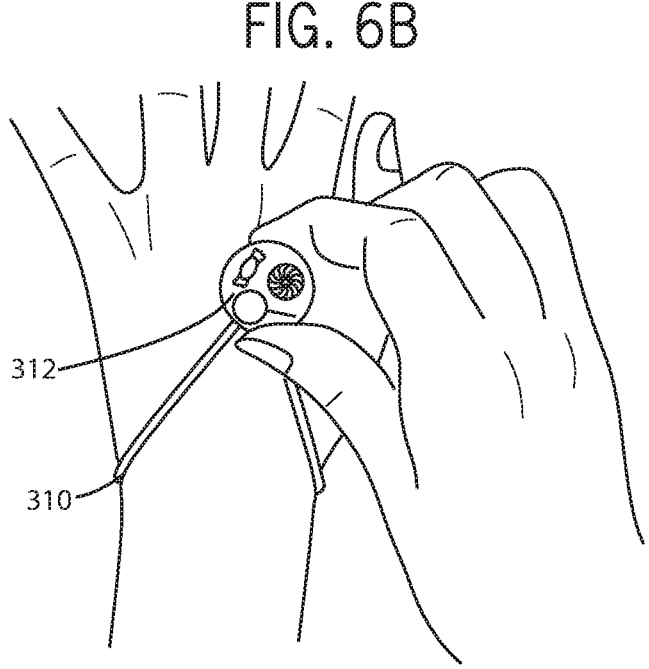
FIG. 6B is an illustration similar to FIG. 6A showing the consumer pulling on the button to activate microencapsulated fragrance.

Referring now to FIGS. 6A and 6B, a hair tie 310 with an attached decorative button 312 is placed around the wrist 314 of a consumer. The decorative button 312 in FIGS. 6A and 6B replaces the pull tag 12 in FIGS. 1 through 5A and 5B as the pull mechanism. Otherwise, the hair tie 310 in FIGS. 6A and 6B is configured and operates similar to hair tie 10 in FIGS. 1 though 5A and 5B.

In the examples shown in FIGS. 7A and 7B through 9, the elastic textile 410, 510, 610 comprises a fabric having elastic properties, such as fabric in which elastic is woven into the fabric. In these embodiments, the elastic fabric should be chosen to have adequate wet pick up to meet the needs of the application, such as an elastic textile blend or spandex.

Figure 7A:
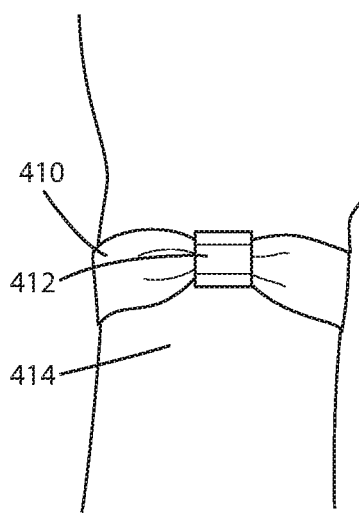
FIG. 7A is an illustration of another example of the invention in which the pull mechanism is a bead that is attached around an elastic ribbon.
Figure 7B:
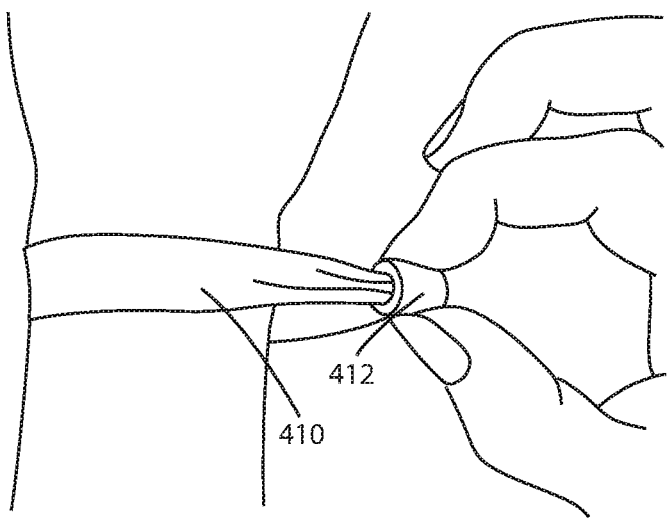
FIG. 7B is an illustration similar to FIG. 7A showing the user pulling on the bead to activate the microencapsulated fragrance.

Referring to FIGS. 7A and 7B, an elastic hair ribbon 410 with a loosely attached bead 412 is placed around the wrist 414 of a consumer. The elastic hair ribbon 410 could also be sold as an elastic wrist band. The bead 412 in FIGS. 7A and 7B replaces the pull tag 12 in FIGS. 1 through 5A and 5B as the pull mechanism. Since the bead 410 is loosely attached, it can move relative to the elastic ribbon/band 410 which enables repeated stretching to occur at a variety of locations. Otherwise, the hair ribbon/wrist band 410 in FIGS. 7A and 7B is configured and operates similar to hair tie 10 in FIGS. 1 and 2 and the hair tie 310 in FIGS. 6A and 6B.

Referring to FIGS. 8A and 8B, an elastic shirt 510 treated with microencapsulated substance with a pull tag 512 is shown being worn by a consumer. The pull tag 512 in FIGS. 8A and 8B is conveniently placed along the arm 51414 of the wearer. FIG. 8A shows the shirt 510 in its natural relaxed state and FIG. 8B shows the wearer pulling on the pull tag 512 to activate microencapsulated substance. The microencapsulated substance can be fragrance, deodorant, insect repellant or a variety of other substances. Also, it is possible to apply more than one microencapsulated substance, e.g. a combination of deodorant and insect repellant. As in the other examples, when the wearer pulls the tag 514, a roughly controlled amount of the microencapsulated substance(s) is released on demand by rupturing, dissolving or melting some of the microcapsule walls or by diffusion through some of the microcapsule walls.

Referring to FIG. 9, an elastic textile 610 made of a poly blend with cotton, nylon, and spandex is treated with microencapsulated substance (e.g. fragrance) and knotted together. The textile in this embodiment is cut to 9" in length and is ½" wide and may contain a design or logo. In this embodiment, the knot 612 serves as the pull mechanism used to stretch the textile and release the fragrance. The band may be worn around the wrist, in the hair, or around the ankle. Such a product may be useful to provide merchandizing samples of perfume to potential customers.

What is claimed is:

1. An apparatus comprising:
an elastic band that includes an elastic core that is surrounded by a fabric;
microencapsulated substance applied to the fabric of the elastic band, wherein the elastic band has a wet pick up of at least 50%;
a graspable pull mechanism attached to the elastic band;
wherein microencapsulated substance is released when the pull mechanism is pulled to stretch the elastic band from a natural relaxed state or a semi-stretched state, and further wherein the pull mechanism is attached to the elastic band so that it can be moved prior to the consumer pulling on the pull mechanism, and consequently activating the microencapsulated substance in a variety of regions of the elastic band.

2. The invention as recited in claim 1 wherein the pull mechanism is a bead connected to the elastic textile so that it can be moved.

3. The invention as recited in claim 1 wherein the microencapsulated substance comprises a fragrance.

4. The invention as recited in claim 1 wherein the microencapsulated substance is insect repellant.

5. The invention as recited in claim 1 wherein the microencapsulated substance is a deodorant.

6. The invention as recited in claim 1 wherein the apparatus is a hair tie.

7. The invention as recited in claim 1 wherein the pull mechanism is a folded over tag attached to the elastic textile by a grommet.

8. The invention as recited in claim 1 wherein the microencapsulated substance is skin safe, non-irritating, and safe for inhalation.

9. The invention as recited in claim 1 wherein the microcapsules are made of melamine resin and are 2-8 microns in size.

10. The invention as recited in claim 1 wherein the surrounding fabric is made of braided nylon thread.

11. The invention as recited in claim 10 wherein the nylon has a thread size of 70D/2.

\* \* \* \* \*